US009827445B2

(12) United States Patent
Cordero Marcos et al.

(10) Patent No.: US 9,827,445 B2
(45) Date of Patent: Nov. 28, 2017

(54) AUTOMATIC CREATION AND SELECTION OF DOSE PREDICTION MODELS FOR TREATMENT PLANS

(71) Applicant: Varian Medical Systems International AG, Zug (CH)

(72) Inventors: María Isabel Cordero Marcos, Espoo (FI); Joona Hartman, Espoo (FI); Esa Kuusela, Espoo (FI); Jarkko Yrjana Peltola, Tuusula (FI); Janne Ilmari Nord, Espoo (FI)

(73) Assignee: Varian Medical Systems International AG, Zug (CH)

( * ) Notice: Subject to any disclaimer, the term of this patent is extended or adjusted under 35 U.S.C. 154(b) by 305 days.

(21) Appl. No.: 14/040,468

(22) Filed: Sep. 27, 2013

(65) Prior Publication Data

US 2015/0095043 A1    Apr. 2, 2015

(51) Int. Cl.
*A61N 5/10* (2006.01)
*G06F 19/00* (2011.01)

(52) U.S. Cl.
CPC ......... *A61N 5/1031* (2013.01); *G06F 19/345* (2013.01); *G06F 19/3481* (2013.01); *A61N 2005/1041* (2013.01)

(58) Field of Classification Search
CPC ....... G06Q 50/22; G06F 19/345; G06F 19/24; G06F 19/3437; G06F 19/3456; A61N 5/1031
USPC .................................................... 705/2, 3, 4
See application file for complete search history.

(56) References Cited

U.S. PATENT DOCUMENTS

| 7,796,731 B2 | 9/2010 | Nord |
| 7,801,270 B2 | 9/2010 | Nord |
| 7,809,107 B2 | 10/2010 | Nord |
| 7,817,778 B2 | 10/2010 | Nord |

(Continued)

FOREIGN PATENT DOCUMENTS

| CA | 2813643 A1 | 4/2012 | |
| WO | WO 2006126109 A1 * | 11/2006 | ............. A61N 5/103 |

OTHER PUBLICATIONS

Zhu, Xiaofeng, "A planning quality evaluation tool for prostate adaptive IMRT based on machine learning," Feb. 2011, Med. Phys. 38(2), pp. 719-726.*

(Continued)

*Primary Examiner* — Mark Holcomb
*Assistant Examiner* — John Go
(74) *Attorney, Agent, or Firm* — Kilpatrick Townsend & Stockton LLP

(57) ABSTRACT

A dose prediction model can be determined for generating a dose distribution of a treatment plan for irradiating a target structure within a patient. Treatment plans from previous patients can be analyzed to determine D characteristic values to obtain a D dimensional point for each treatment plan. The treatment plans can be clustered based on the D dimensional points. The treatment plans of a cluster can then be used to determine a dose prediction model. A dose prediction model for patient can be selected from among multiple models. Characteristics about the patient can be used to determine a D dimensional point corresponding to the patient. The D-dimensional point can be used to select a model in comparison to D dimensional points of the models.

20 Claims, 8 Drawing Sheets

(56) References Cited

U.S. PATENT DOCUMENTS

| | | |
|---|---|---|
| 8,009,804 B2 | 8/2011 | Siljamak |
| 8,085,899 B2 | 12/2011 | Nord |
| 8,331,532 B2 | 12/2012 | Nord |
| 2003/0177039 A1* | 9/2003 | Nicholas ............... G06Q 50/22 705/2 |
| 2005/0131738 A1* | 6/2005 | Morris ................. G06F 19/322 705/2 |
| 2009/0154644 A1* | 6/2009 | Nord ...................... A61N 5/103 378/65 |
| 2009/0240523 A1* | 9/2009 | Friedlander ........ G06F 19/3443 705/2 |
| 2009/0299766 A1* | 12/2009 | Friedlander ........... G06Q 10/00 705/3 |
| 2010/0204920 A1 | 8/2010 | Dranitsaris et al. |
| 2010/0303205 A1* | 12/2010 | Kapoor ............... A61N 5/1048 378/65 |
| 2011/0082712 A1* | 4/2011 | Eberhardt, III ..... G06F 19/3437 705/4 |
| 2011/0106749 A1 | 5/2011 | Krishnan et al. |
| 2012/0016690 A1 | 1/2012 | Ramarajan et al. |
| 2012/0136194 A1 | 5/2012 | Zhang et al. |
| 2012/0310615 A1* | 12/2012 | Moore ............... G06F 19/3437 703/11 |
| 2013/0077752 A1* | 3/2013 | Zankowski .......... A61N 5/1031 378/65 |
| 2013/0085343 A1 | 4/2013 | Toimela et al. |

OTHER PUBLICATIONS

Zhu, Xiaofeng, "A planning quality evaluation tool for prostate adaptive IMRT based on machine learning," Med. Phys. 38(2), Feb. 2011.*

U.S. Appl. No. 14/040,479 (unpublished), filed Sep. 27, 2013, entitled "Decision Support Tool for Choosing Treatment Plans," 39 pages.

Yuan, Lulin, et al., "Quantitative analysis of the factors which affect the interpatient organ-at-risk dose sparing variation in IMRT plans," Med. Phys., Nov. 2012, vol. 39, No. 11, pp. 6868-6878.

Appenzoller, Lindsey, M., et al., "Predicting dose-volume histograms for organs-at-risk in IMRT planning," Med. Phys., Dec. 2012, vol. 39, No. 12, pp. 7446-7461.

International Search Report and Written Opinion dated Mar. 6, 2015 in PCT/IB2014/064936, 11 pages.

Office Action dated Jul. 31, 2015 in U.S. Appl. No. 14/040,479, 15 pages.

U.S. Appl. No. 14/040,479, "Final Office Action", dated Dec. 23, 2016, 26 Pages.

U.S. Appl. No. 14/040,479, Non-Final Office Action dated May 19, 2016, 23 pages.

* cited by examiner

AUTOMATIC CREATION AND SELECTION OF DOSE PREDICTION MODELS FOR TREATMENT PLANS

CROSS-REFERENCES TO RELATED APPLICATIONS

This application is related to commonly owned and concurrently filed U.S. patent application entitled "Decision Support Tool For Choosing Treatment Plans" by Hartman et al., the disclosure of which is incorporated by reference in its entirety.

FIELD

The present disclosure relates generally to treatment planning for radiation therapy and is more particularly directed to dose prediction models for generating a treatment plan.

BACKGROUND

In general, radiation therapy consists of the use of ionizing radiation to treat living tissue, usually tumors. There are many different types of ionizing radiation used in radiation therapy, including high energy x-rays, electron beams, and proton beams. The process of administering the radiation to a patient can be somewhat generalized regardless of the type of radiation used.

Techniques allow the radiologist to treat a patient from multiple angles while varying the shape and dose of the radiation beam, thereby providing greatly enhanced ability to deliver radiation to a target within a treatment volume while avoiding excess irradiation of nearby healthy tissue. However, this variability in delivering radiation has made the task of developing treatment plans more difficult. Both the target within the treatment volume and any nearby organs may have complex three dimensional shapes adding to the difficulty of preparing a treatment plan.

Treatment planning can start with (1) images of the treatment volume (e.g., slices from CT or MRI scans) and, (2) the desired dose of radiation which is to be delivered to a target, such as a tumor, within the treatment volume, and (3) the maximum dose which can be safely absorbed by tissue structures, such as organs, within the treatment volume that are adjacent to or near the tumor or other target volume. A variety of algorithms have been developed to solve the "inverse problem" of devising and optimizing a specific, three-dimensional treatment plan for irradiating the treatment volume from a variety of angles or, in arc therapy, while the system gantry is moving, to deliver a desired radiation dose to the target while minimizing irradiation of nearby tissue, taking into account the capabilities and physical limitations of the radiotherapy system. Generally speaking, the inverse problem involves optimizing the angles, MLC leaf movements and durations of irradiations. Because of the large number of variables involved and complex matrix manipulations that are required, the algorithms for calculating and optimizing treatment plans require substantial computational time even when using modern high speed computers.

However, the desired dose may not always be possible given the constraints of the system and the particular patient (e.g., geometry of the tumor). Thus, the desired dose distribution may need be modified as part of the optimization process, which can cause further difficulty. Therefore, it is desirable to identify a dose distribution that is achievable.

In knowledge based dose prediction, information from previously planned radiation treatments are used to gain knowledge about what is an achievable dose distribution in a new case. One approach to knowledge based dose prediction is to use a set of the previously planned cases to create a prediction model that is then be used (without needing to store all information related to this training set) to predict the dose for a new case. The dose prediction model can help identify a dose distribution that is achievable and reduces the effort to determine a desired dose.

Currently, dose prediction models are created from training sets of treatment plans that are selected by a human operator. It may prove very time consuming for a human operator to shift through thousands of treatment plans in order to categorize them into different training sets for different models. It is also very difficult for a human operator to evaluate whether all selected treatment plans in a particular training set are representative of the set.

Further, when many predictive models exist, it is difficult to manually select the prediction model that would be most valid for a current patient. Additionally, a user can only choose the model for the current plan from the existing pre-configured models, none of which may provide an accurate prediction for the dose distribution.

Therefore, it is desirable to provide new methods to create and select dose prediction models.

BRIEF SUMMARY

Embodiments of the present invention are directed to determining a dose prediction model for generating a dose distribution of a treatment plan for irradiating a target structure (e.g. a tumor) within a patient. Treatment plans from previous patients can be analyzed to determine D characteristic values, e.g., geometric characteristics of the tumor. Coordinates can be assigned to the D characteristic values to obtain a D-dimensional point for each treatment plan. The treatment plans can be clustered based on the D-dimensional points. The treatment plans of a cluster can then be used to determine a dose prediction model for generating one or more new treatment plans. In this manner, the creation of a dose prediction model is more efficient than selecting treatment plans by hand, and greater accuracy can be achieved, e.g., via specified criteria for clusters.

Embodiments of the present invention are also directed to selecting a dose prediction model for generating a dose distribution of a treatment plan for irradiating a target structure within a patient. Characteristics about the patient can be used to determine a D-dimensional point corresponding to the patient. The D-dimensional point can be used to select a model from K models. For example, a set of data for each model can be used to determine at least one D-dimensional point for each model (e.g., a centroid for each cluster corresponding to a model). The D-dimensional point of the patient can be compared to the D-dimensional points of the models to selected a model, which can be used to determine a treatment plan for the patient.

Other embodiments are directed to systems and computer readable media associated with methods described herein.

A better understanding of the nature and advantages of embodiments of the present invention may be gained with reference to the following detailed description and the accompanying drawings.

DEFINITIONS

Figure 1:
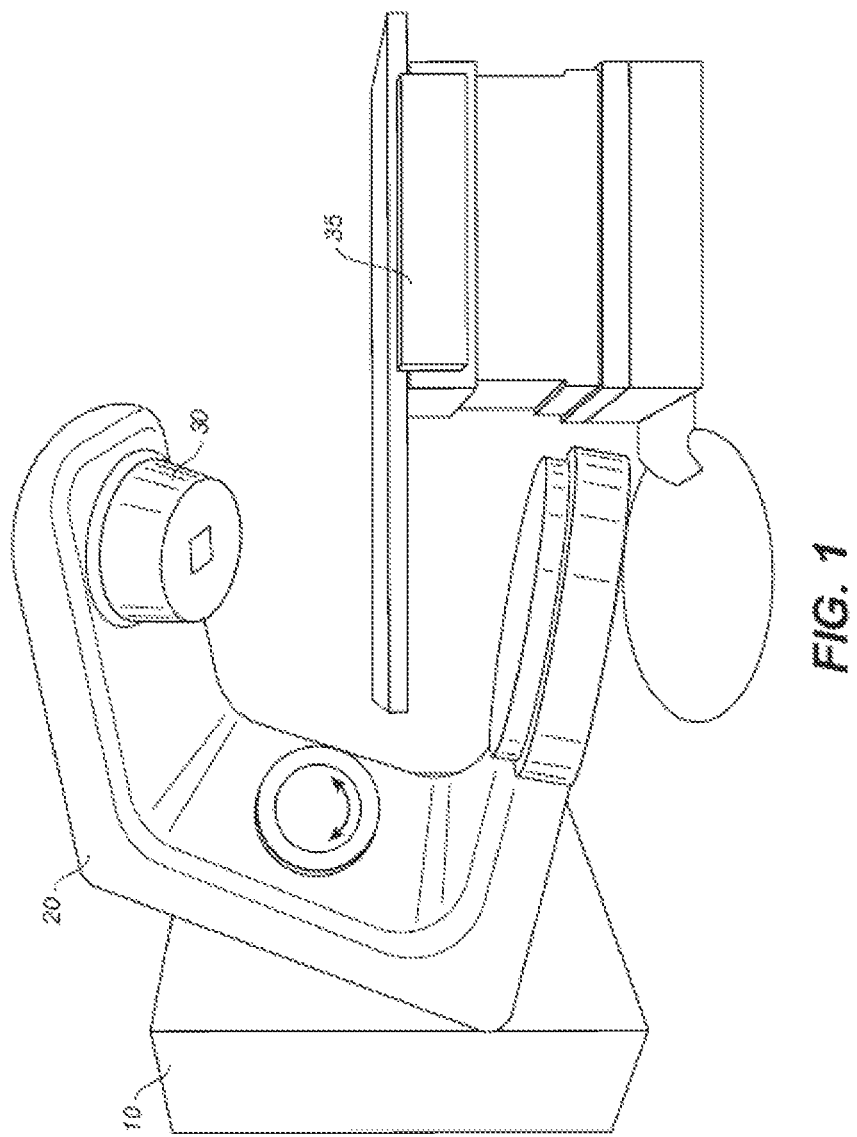
FIG. 1 is a perspective view of a radiation therapy system.

"Radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose.

A "treatment plan" can include a dose distribution, machine parameters for achieving the dose distribution for a given patient, and information about the given patient. A dose distribution provides information about the variation in the dose of radiation with position. A "dose distribution" can take many forms, e.g., a dose volume histogram (DVH) or a dose matrix. A DVH can summarize three-dimensional (3D) dose distributions in a graphical 2D format, e.g., where the horizontal axis is the dose (e.g., in units of grays—Gy) absorbed by the target structure (e.g., a tumor) and the vertical axis is the volume percentage. In a differential DVH, the height of a bar at a particular dose indicates the volume of the target structure receiving the particular dose. In a cumulative DVH, the height of a bar at a particular dose represents the volume of the structure receiving greater than or equal to that dose. The cumulative DVH is generally a curve (e.g., when small bin sizes are used), whereas the differential DVH is generally a disjoint bar graph. A drawback of a DVH is that it offers no spatial information; i.e., a DVH does not show where within a structure a dose is received. A dose matrix can provide the dose that each part of the body receives.

A "dose prediction model" receives patient data and outputs a dose distribution that is predicted to be obtainable. A model can also output other data, such as optimization objectives. Different types of radiation treatments can have different models. The patient data can include diagnostic information (e.g., general tumor location or stage information) and geometric information (e.g., the spatial geometry of the tumor and of other organs in the patient). A particular model can have an accuracy (reliability) associated with the predicted dose distribution. The accuracy can be determined from a set of test treatment plans whose dose distribution has been determined via other means (e.g., by optimizing a cost function). For example, the accuracy can be determined based on how well the model predicts the actual dose distributions obtained by optimizing a cost function.

DETAILED DESCRIPTION

A dose prediction model can be used to determine a dose distribution for a new patient. In one embodiment, the dose prediction models can already be determined. For example, a plurality of pre-determined models may be created based on training sets of previously determined treatment plans for other patients. Embodiments can automatically select the treatment plans to be used in creating a dose prediction model. The automatic selection can be based on a similarity of defined characteristics between treatment plans, as quantified by a distance. A training set can then be used to determine a model, which can be used to generate a treatment plan for a new patient.

Regardless of how a model is created, an embodiment can select a best model between pre-existing models. For example, characteristics of the treatment plans of the training set used to create the model can be saved as characteristics of the model, and then used to determine if the new patient data is similar to the characteristics of the model. This can be done across a plurality of dose prediction models to determine which model is most similar. The characteristics of the treatment plans of a model can be saved in a variety of ways, e.g., as an average of the characteristics of the treatment plan, as a volume, or as the raw data of the specific treatment plans in the training set of the model.

Additionally, embodiments can create a dose prediction model that is tailored to a new patient. Treatment plans with similar characteristics as the new patient can be identified and then used to create a prediction model for the new patient.

I. Treatment System

Figure 2:
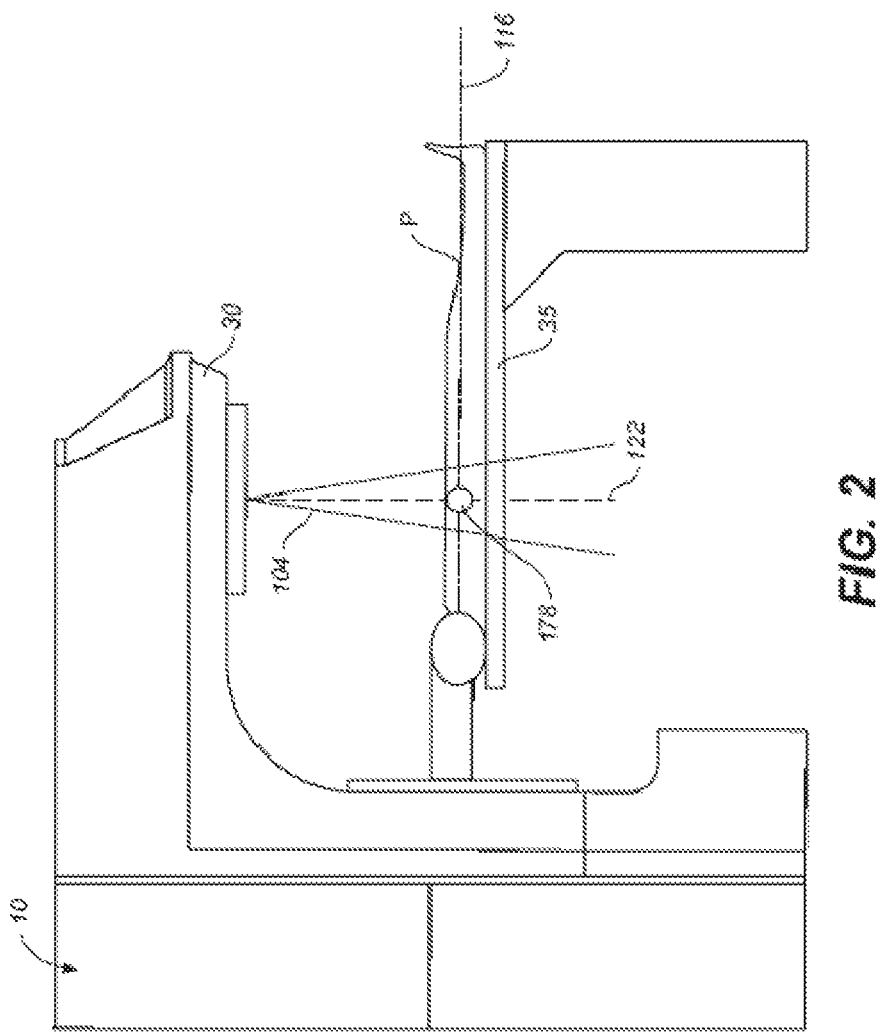
FIG. 2 is a side view of a radiation therapy system.

FIGS. 1 and 2 depict a radiation therapy system of the type which may be used in connection with the present invention. Referring to FIG. 1, a perspective view of radiation therapy system (in this case a linear accelerator) is shown. Typically, such a system is capable of generating either an electron (particle) beam or an x-ray (photon) beam for use in the radiotherapy treatment of patients on a treatment table 35. Other radiation therapy systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) which includes operational electronics for controlling the different modes of operation of the accelerator. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 2, a somewhat more detailed side view of a radiation therapy system of the type which may be used in connection with the present invention is shown. A patient P is shown lying on treatment table 35. X-rays formed as described above are emitted from the target in treatment head 30 in a divergent beam 104. Typically, a patient plane 116, which is perpendicular to the page in FIG. 1B, is positioned about one meter from the x-ray source or target, and the axis of gantry 20 is located on plane 116, such that the distance between the target and isocenter 178 remains constant when gantry 20 is rotated. Isocenter 178 is at the intersection between patient plane 116 and the central axis of beam 122. A treatment volume to be irradiated is located about the isocenter.

"Jaws" (not shown) or x-ray collimators comprising an x-ray blocking material, are positioned in head 30 to define the width of the x-ray beam at the patient plane. Typically, the jaws are moveable and, when fully open, define a maximum beam of about 40 cm×40 cm at patient plane 116. A multileaf collimator ("MLC") (not shown in FIG. 1B) is positioned at the exit of head 30, to further shape the x-ray beam. Since its introduction in 1990 the MLC has become a standard feature of most radiation therapy systems. Current MLCs sold by the assignee of the present invention use up to 120 individually controllable leaves, typically thin slices of tungsten, that can be moved into or out of the x-ray beam under the control of system software. The MLC can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to the isocenter in the path of the x-ray beam, is defined by the jaws, the angle of the head and the MLC. In IMRT the leaves of the MLC are moved, such that the treatment volume comprises the total volume exposed during the course of a treatment. In arc therapy, the gantry is moved while radiation is delivered.

Modern radiation therapy techniques involve the use of a treatment plan designed to irradiate a desired target volume, usually corresponding to a tumor, with a desired dose of x-rays (or other radiation). Most treatment planning involves the use of the MLC to provide conformal and/or intensity modulated irradiation. Generally speaking, a treatment plan comprises irradiating one or more selected portions of the treatment volume with a calculated dose of x-rays, and often involves irradiating a treatment area from a plurality of different angles which, in the case of arc therapy, may be delivered while the gantry is rotated. Various treatment planning software and other tools are available for developing specific treatment plans, and the details of the various techniques for creating such plans are known and will be described in further detail below. Again, generally speaking, after a treatment plan is created it is implemented, in part, by controlling the angle of incidence and the leaves of the MLC so as allow the desired radiation dose to reach the selected portions of the treatment volume from the selected angles or while the gantry is rotating. In the simplest type of treatment plan, the MLC is adjusted to provide static conformal irradiation of a specific site from a single angle. In more complex plans, the leaves are moved into different positions between or during irradiations. The leaves of the MLC can either be moved iteratively into different positions while the beam is off, with irradiation between movements, (such that the leaves are static during x-ray emission), or they can be continually moved during irradiation in a "sliding window" or other variable aperture technique. As noted above, an important aspect of the conformal and IMRT techniques that are associated with the use of MLCs is the ability to both provide a desired dose of radiation to a target volume while minimizing the dose delivered to adjacent healthy tissue.

As described in more detail in the Background section above, several techniques have been developed to create treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a treatment plan. Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk that can only receive a much lower, maximum prescribed amount of radiation without risk of damage. This volumetric information along with the prescribed dose limits and similar objectives set by the medical professionals is the basis for calculating an optimized dose distribution and the treatment plan to deliver it. The volumetric information may, for example, be reduced to an objective function or a single figure of merit that accounts for the relative importance of various trade-offs inherent in such a plan, along with constraints that must be met for the plan to be medically acceptable or physically possible.

Treatment planning algorithms can account for the capabilities of the specific radiation therapy system they are used with. For example, the type, energy level and fluence of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

II. Selection of Training Set for Determining a Model

As mentioned above, identifying a training set of treatment plans for creating a dose prediction model can be time-consuming and difficult. In some embodiments, the treatment plans of a training set can be automatically selected based on characteristics of the treatment plans. For example, a heterogeneous group of radiotherapy treatment plans can be analyzed with regards to certain characteristics of the plans and clustered into groups (training sets), where the treatment plans of a training set have similar characteristics. As another example, a training set can be determined based on data of a new patient.

Figure 3:
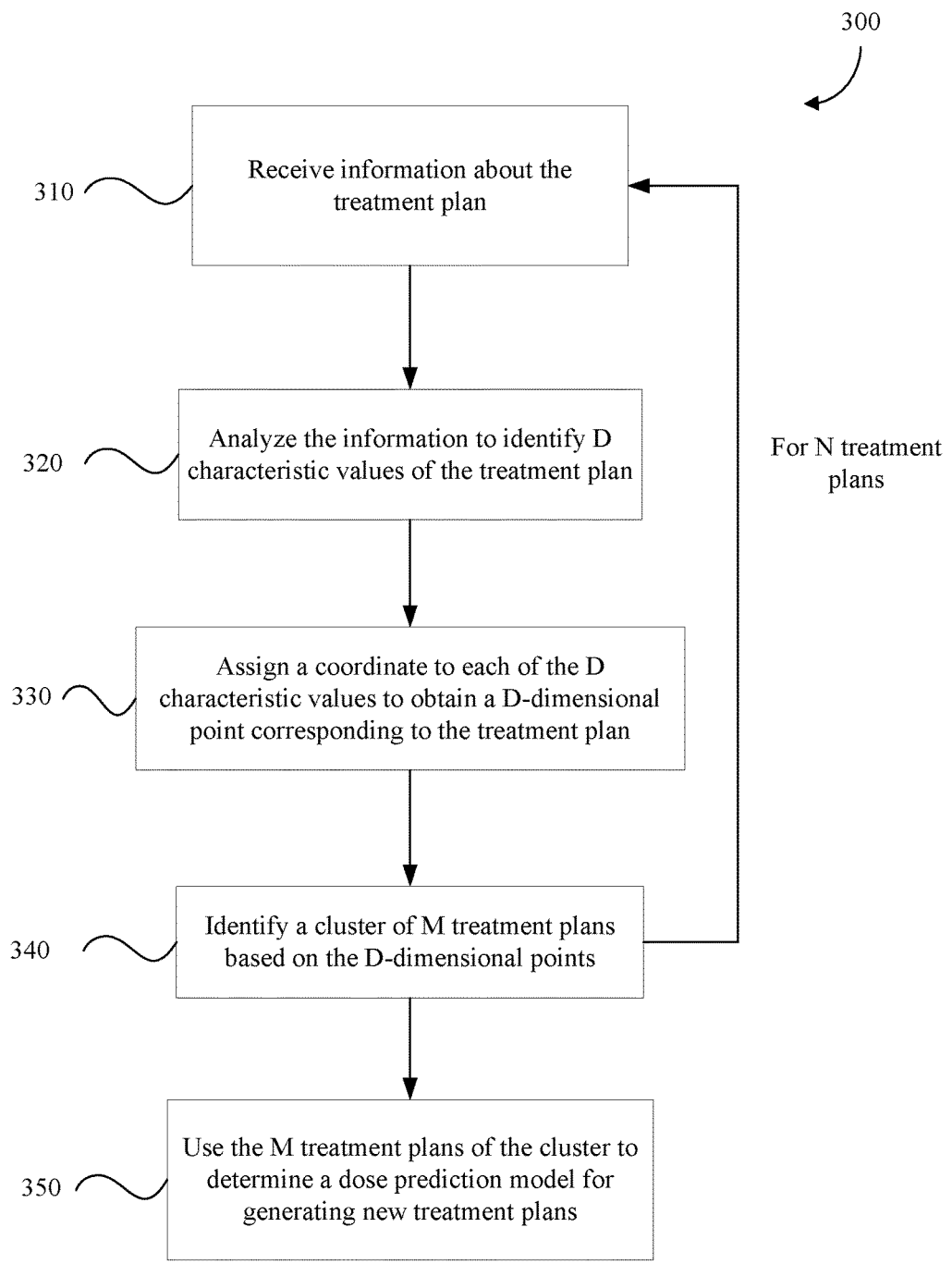
FIG. 3 is a flowchart of a method 300 of determining a treatment plan for irradiating a target according to embodiments of the present invention.

FIG. 3 is a flowchart of a method 300 of determining a treatment plan for irradiating a target according to embodiments of the present invention. Method 300 can be performed wholly or partially with a computer system, as can other method described herein. Blocks 310-340 are repeated for each of N treatment plans corresponding to a plurality of patients. The patients can be considered former patients as a treatment plan has already been developed. Each treatment plan can correspond to a different patient, but more than one treatment plan can be for the same patient.

At block 310, information about the treatment plan is received. For example, the information about the treatment plan can include information about a patient for whom the treatment plan was designed. The information can also include a dose distribution for the treatment plan, as well as the machine parameters for obtaining the dose distribution.

At block 320, the information is analyzed to identify D characteristic values of the treatment plan. Each characteristic value corresponds to a different characteristic of the treatment plan. The D characteristic values can include one or more geometric characteristic values of a tumor of the patient. The D characteristic values can act as a set of criteria for determining a similarity among the treatment plans.

Examples of characteristics include characteristics that describe the patient geometry (e.g., mass, volume, a particular size, such as length, width, and depth) and the geometric relationship of the target structure and healthy tissue (e.g., a physical distance between the two, a type of healthy tissue, a number of critical organs around the target, etc.). Other examples for characteristics related to a patient may include diagnostic information (such as the type of tumor or general location, and the stage of the tumor) and relevant clinical and demographic data such as patient's sex and diagnosis. Besides patient-related characteristics, characteristics of the field geometry and dose distribution used to irradiate the patient can be used.

At block 330, a coordinate is assigned to each of the D characteristic values to obtain a D-dimensional point corresponding to the treatment plan. The coordinate can simply be the corresponding characteristic value (e.g., a number specifying a mass or volume of a tumor). The assigning of a tumor can also include a transformation, e.g., two possible classifications of a characteristic (e.g., a diagnosis or radiation type) can be assigned to be 0 or 1.

Each characteristic can correspond to a different dimension in a D-dimensional space. The number of possible values for any given dimension may be just two (e.g., just two options) or have more than two. In the limit of many options, the possible values can effectively be continuous values (e.g., numerical values), as opposed to discrete values (e.g., only two or ten options).

At block 340, a cluster of M treatment plans is identified based on the D-dimensional points. M would be less than N. Accordingly, the N treatment plans can be organized into M groups (clusters), where each cluster can include a plurality of treatment plans. The treatment plans in a cluster would generally have similar values for the D characteristics. A distance between D-dimensional points can be used to determine whether treatment plans are in a same cluster. The clusters can be identified in a variety of ways, as is mentioned herein.

All the M treatment plans of the cluster can be required to have the same value for particular characteristic(s). For example, all M treatment plans can be constrained to be for the same diagnosis (e.g., liver cancer). Other characteristics can have a distance measured between the characteristic values (e.g., size, shape, and location of the tumor). For instance, the size or volume of the tumor (e.g., one cubic centimeter or two liters) can be numerical values, with a distance between two values. The cluster can be determined such that the tumor size and locations are similar (e.g., a distance between the D dimensional points is within a threshold, which may be determined dynamically).

A distance can be computed as a sum of differences between values for the various dimensions, e.g., of ones which are not constrained to be equal. The distance can include different weightings for different dimensions (e.g., one characteristic can be weighted higher than another distance). For example, a distance between two treatment plans can have a difference of a first characteristic (dimension) multiplied by a first weight and a difference of a second characteristic (dimension) multiplied by a second weight. A difference between two values can be based on subtraction of numerical values. As another example, any difference between two values can be designated as having a same difference value (e.g., when a type of tumor differs, the difference can always be designated as one).

In one embodiment, the cluster can be determined dynamically based on information for a new patient. As the cluster specifically determine for the new patient, this embodiment is called real-time modeling. In another embodiment, the cluster is determined from only previous treatment plans. Multiple clusters can be determined from the entire collection of previous treatment plans. Various clustering algorithms can be used, such as a k-means algorithm.

At block 350, the M treatment plans of the cluster are used to determine a dose prediction model for generating one or more new treatment plans. The cluster can be used as the training set for determining the dose prediction model. In one embodiment, the dose prediction model can be used to generate a new treatment plan by outputting a predicted dose distribution, which is then used to obtain machine parameters for obtaining the dose distribution. The machine parameters can be determined by optimizing a cost function. The dose distribution can also be updated during this optimization process. The one or more new treatment plans can be generated for one or more new patients. A new treatment plan can be used for irradiating a target structure within the patient.

A. Characteristic Values (Patient Data)

Various types of data can be used to determine the characteristic values. For example, the treatment plan data could comprise a diagnosis for the patient. Thus, a similar diagnosis may be found in the treatment plans of a cluster. A size of a patient (e.g., mass or height) and tumor size may also provide a similar the dose level at the target, and thus may be used as characteristics. A distance from critical organs can also be used to identify matches in the geometry patterns of the patients corresponding to the respective treatment plans. General information about the patient can also be used, e.g., demographic information, such as ethnicity or some genetic measure (e.g., a DNA profile).

In one embodiment, each treatment plan can be stored as a record in a database, with a plurality of fields for the record. The fields can correspond to any of the above-mentioned characteristics. Such information can be entered into the database when a treatment plan for patient is created. Any of the fields can have numerical values or character values, e.g., the character values correspond to particular classifications, such as a diagnosis or stage of the tumor. Which fields are to be used as the characteristics for determining a cluster can be set as a default will be chosen by a user. Once the fields have been chosen, a record of the treatment plan can be stored as a D-dimensional point. The plurality of D dimensional points can then be fed into a clustering function. In one implementation, such fields can be searched to identify treatment plans having certain characteristics. The database and any engine for performing methods described herein may be implemented in a server and accessed from a client.

B. Using Dose Distribution as a Characteristic Value

The information about the treatment plans can be obtained from a set of patient cases for which treatment plans have already been determined. Since the treatment plans are already determined, the dose distributions of the treatment plans can also be used as one of the characteristics for determining a similarity among the treatment plans. Accordingly, in one embodiment, the D characteristic values corresponding to a treatment plan include a dose distribution of the treatment plan. Accordingly, embodiments can find clusters of similar treatment plans automatically from a database by considering the similarities in patient geometry and the dose distribution compared to other treatment plans.

One or more specific values can be determined from a dose distribution, and each of the specific values can be used as a characteristic (dimension). Any term (e.g., statistical terms) determined from a dose distribution can be used. For example, first order terms such as maximum dose, mean dose, median dose, minimum dose, dose in a specific volume percent, and volume percent of a specific dose may be used. Second or higher order terms of the first order terms (e.g., standard deviation, skewness, and kurtosis) are other examples. Other examples include projections of DVHs over principal components (i.e. principal components scores).

C. Determination of Dose Prediction Model

Once a cluster of similar treatment plans (e.g., including patient data) have been found, one can make an estimate of the dose distribution for a new patient that has similar characteristics as the treatment plans of the cluster. In one embodiment, the estimate of the dose distribution for new patient can be determined as an average or weighted average of the dose distributions of the treatment plans in the cluster. As a simple example where the cluster has two treatment plans, if the D-dimensional point for the new patient is halfway between the two treatment plans, then the estimated dose distribution can be an average of the dose distributions of the two treatment plans. If the D dimensional point for new patient was closer to one treatment plan of the other, then a weighted average might be determined. In one implementation, the average can be done on a per bin basis (i.e., the average is of the volume fraction for each dose range). Accordingly, the model can be defined by the rules for determining such an average.

In another embodiment, the dose prediction model can be determined from a functional fit. The parameters of such a functional fit can be stored, and the individual characteristics of the treatment plans of the training set can be discarded. Such a dose prediction model can receive the characteristic values of a new patient (e.g., as a new D-dimensional point) and output the dose distribution. The values of the dose distribution may be parameterized to provide the predicted values for each dose range of a dose volume histogram (DVH). Thus, the dose prediction model can provide discrete values for each dose range of a DVH.

Figure 4:
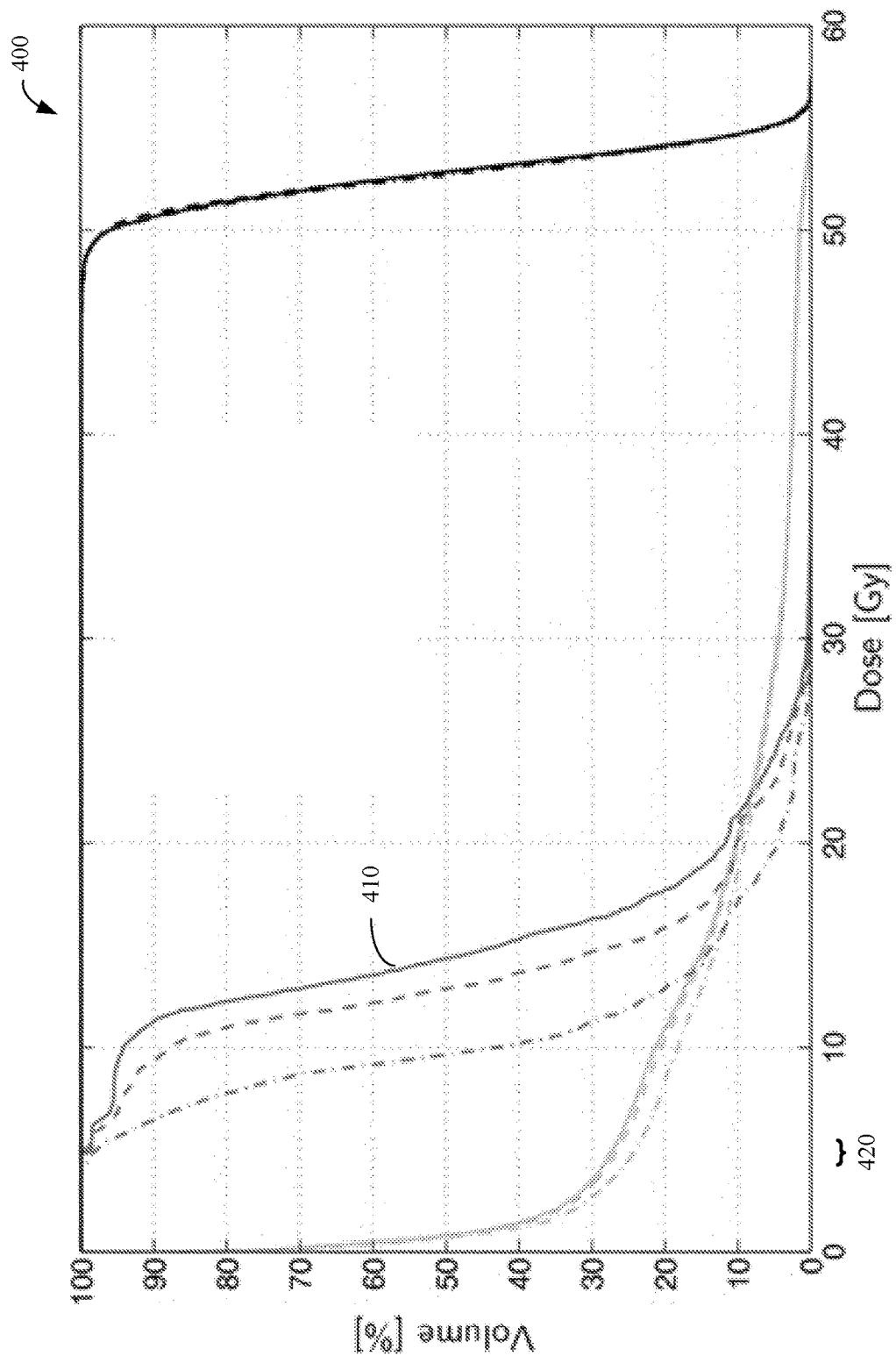
FIG. 4 shows a plot 400 of a plurality of dose volume histograms (DVH) according to embodiments of the present invention.

FIG. 4 shows a plot 400 of a plurality of dose volume histograms (DVHs) according to embodiments of the present invention. The horizontal axis provides an amount of radiation in Grays. The vertical axis is the percentage of volume. The dose distributions represent the volume of the structure receiving greater than or equal to that dose. For example, distribution 410 has about 50% of the volume receiving 15 Grays or more. The curves can be broken up into various bins (dose ranges). For example, dose range 420 is about one Gray wide. Dose distributions can be compared to one another at a resolution of the bin size, e.g., a difference between two distributions can be computed for each dose range.

In one implementation, as part of the process of determining the dose prediction model, some of the characteristics can be dropped in order to provide more accurate model. For example, if a selection criterion that tumor size is very well matched for cluster, one may drop the size of the tumor as a parameter from the modeling because you would already know that it matches very well. This may improve the model as the small differences in tumor size can provide for relatively flat objective function in the dimension of tumor size, which can cause difficulties in determining the functional fit.

The determination of the dose prediction model can also account for other factors, such as not providing too much radiation to healthy tissue. For example, after some fraction of the organ gets some level of dose, side effects will be seen, and this can be discouraged in the determination of the model.

D. Generation of Treatment Plans Using Dose Prediction Model

As mentioned above, the dose prediction model can be used to determine a predicted dose distribution for patient. The predicted dose distribution can be used to set optimization objectives that will drive the optimization algorithm towards the solution found. The predicted dose distribution can also be used to determine if other treatment plans (e.g., other than radiation or other type of radiation) would be better or if there is a need to sacrifice some organ in order to spare a more important organ. The predicted dose distribution can be used, as well, as a quality tool to evaluate if, for example, for a manual planned case there would be a better solution.

In one embodiment, a model outputs the estimated achievable DVH (e.g., as a 2D representation of the dose) and optimization objectives to guide the optimization algorithm towards that solution. The optimizer can calculate an optimized 3-D dose distribution and the field fluences (intensity of dose delivered in "individual" beams of radiation) that can be obtained with the 3D dose distribution. The field fluences can be used to calculate the MLC movements in IMRT (in arc cases they are calculated concurrently). The fluences and MLC movements can be input to the dose calculation algorithm that calculates the real dose that would be delivered to the patient given the plan.

III. Refinement of Dose Prediction Model

In addition to determining the dose prediction model itself, an accuracy (effectiveness) of the model can be determined. For the training set, the actual treatment plans are available. Embodiments can compare the result of the model to the actual plans. This accuracy can also be used to refine the treatment plans in a cluster, and thus refine the dose prediction model.

A. Accuracy/Validation

In one embodiment, the predicted dose distributions output from the model can be tested by comparing the predicted dose distributions to the actual dose distributions of select treatment plans. The selected treatment plans used for testing can include all or some different treatment plans from the ones in the training set, or all can be from the training set. For example, patient data of a treatment plan from the training set can be input to the model to obtain a predicted dose distribution, which can be compared to the actual dose distribution of the treatment plan. This comparison can provide a measure of accuracy of the model, e.g., as a reliability score. Examples of reliability scores include the number of histogram bins that are overestimated, number of histogram bins that are underestimated, average over/under estimation, root mean square error (RMSE) per bin, and total RMSE of the estimate.

The comparison can be performed for multiple test treatment plans, and the accuracy (reliability score) can be determined as an average or some of the errors between each of the predicted and actual dose distributions. The errors can be calculated as a difference between the volume fractions for each dose range. This measure of accuracy can be stored with the model for use in later evaluations of the model. The test treatment plans can be determined in a similar manner as the training set, and can even be the same as the training set.

The measure of accuracy can be compared to a threshold value for determining whether the model is sufficiently accurate. Accordingly, a testing set of selected treatment plans can be used to compare dose predictions of the model to the actual dose distributions of the testing set plans as part of a validation of a model. If the model is not sufficiently accurate, the model can be refined in various ways, e.g., updating parameters of the model. The model may have specific functional form with parameters that can vary to fit the model to the data of the cluster. The parameters can be updated so as to increase the accuracy of the model for the testing set plans. In this manner, the model (i.e., the parameters for the model) that most accurately predicts the dose distributions of a testing set is indicated.

In another embodiment, different functional forms for the model may be used and that accuracy can be compared to each other to determine the most accurate model. Thus, one can make trial predictions with several models to establish which model can most accurately predict a certain cluster of treatment plans.

In addition to testing an accuracy of the model, a success rate of the dose distribution can also be tracked. For example, if a first treatment plan was more successful in treating a tumor than another treatment plan (e.g., as determined by a physician), then the first treatment plan can be weighted higher in a functional fit process for determining the dose prediction model. In this manner, the predicted dose distributions can provide more successful treatment plans. Success can be measured in a variety of ways, e.g., by reduction in size of tumor, length of remission, side of effects, etc.

As another example for determining a reliability of a model, one can calculate a metric for each dimension of a data point to identify if the point in that dimension is an outlier or not (e.g., with z-metrics or z-modified metrics). Acceptable values for certain dimensions of the training set can be identified to determine whether the data point for a new patient is outside the acceptable values. Patient (data points) of a training set can also be eliminated if they are outliers. Other metrics can consider a subset of dimensionalities, distance metrics, etc. Such a process can identify when a particular characteristic for a patient (or treatment plan) is significantly different than the characteristics of the patients used for the model. If there is a significant difference, the reliability may decrease, and thus that model may not be used or may need to be modified. The level of decrease can depend on the particular characteristic and the extent of the difference. For example, a model may only be accurate for particular range of values for that particular characteristic, thereby causing errors in the prediction for a patient having a characteristic outside the operating range.

Reliability scores can also be determined for dose matrices. For example, consider the dose matrix as an image of size XY and dimensionality Z. Image processing methods can be used to extract features that will allow the calculation of distances (an RGB image can be considered dimension 3 while a black-and-white can be considered dimension 1, where dimensionality z can then be used). As another example, the dose matrix can be summarized into 2D vectors, such as the DVHs or distance DVHs, for each of the structures. Metrics can be compared between them (e.g., using signal processing methods). Checking estimates of prescribed doses can also be used.

In one embodiment, dose metrics can be used to calculate the DVH of each of the structures, and the maximum dose can be calculated. The DVHs can be further processed to obtain the first 2-3 principal components (e.g., using a machine learning algorithm for principal component analysis). From the principal components and the DVHs, the principal component scores can be calculated. These principal component scores can be used to check how similar treatment plans are.

B. Updating Plans in Cluster

Accuracies and errors of a model can be used to iteratively create new models by subdividing or combining models (e.g., by subdividing or combing training sets) until certain acceptance thresholds are met. Additionally, specific treatment plans can be identified for excluding from the cluster. For example, the predicted dose distribution for a particular treatment plan have a large difference from the actual dose distribution. This treatment plan can be identified as not being representative of the cluster. Thus, one embodiment can identify individual plans of a training set (cluster) that are not representative of a model and exclude these plans. The remaining plans can then be used in a new iteration for determining the model.

Figure 5:
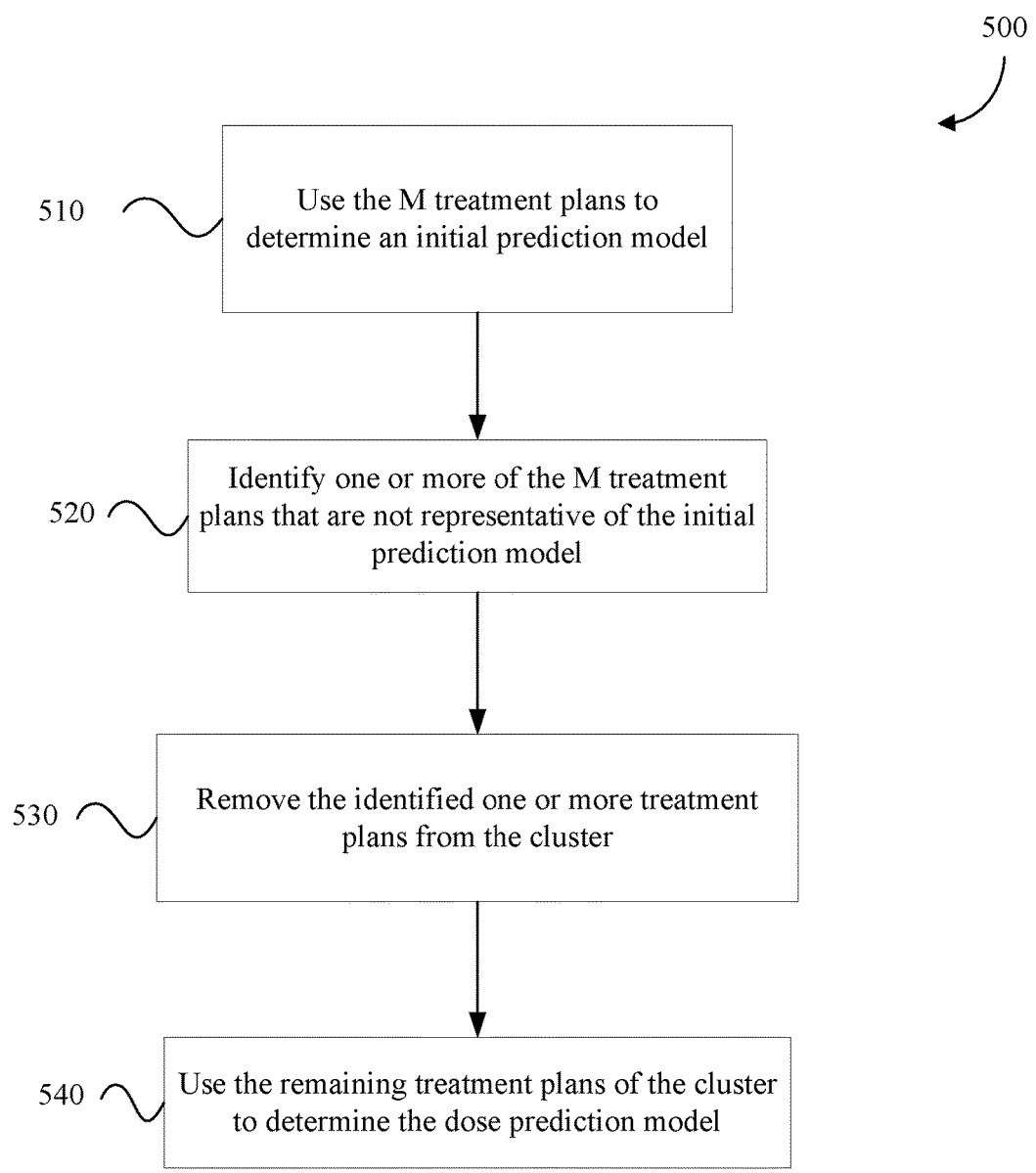
FIG. 5 is a flowchart illustrating a method 500 for determining a dose prediction model using M treatment plans according to embodiments of the present invention.

FIG. 5 is a flowchart illustrating a method 500 for determining a dose prediction model using M treatment plans according to embodiments of the present invention. Method 500 may be used to refine the treatment plans within a cluster in order to provide better dose prediction model.

At block 510, the M treatment plans are used to determine an initial prediction model.

Initial prediction model can be determined as described above. In some embodiments, the method for determining the initial prediction model can be different than the method for determining the final dose prediction model.

At block 520, one or more of the M treatment plans that are not representative of the initial prediction model are identified, e.g., as described above for identifying outliers. In one embodiment, one can identify treatment plans where the predicted dose distribution is very different from the actual dose distribution that was determined for the treatment plan. These treatment plans having a high error can be identified as not being representative of the model. Such exclusion step can occur after multiple iterations in updating parameters of the model so that an additional improvement in the accuracy is not expected for these non-representative treatment plans. Such non-representative treatment plans might occur when a doctor specifies very unique criteria for a treatment plan.

At block 530, the identified one or more treatment plans are removed from the cluster. The identified one or more treatment plans can simply be excluded from the next step in an iterative process for determining the dose prediction model. In one embodiment, any rates associated with the identified one or more treatment plans can be reduced, thereby effectively providing an exclusion of the treatment plan from the cluster.

At block 540, the remaining treatment plans of the cluster are used to determine the dose prediction model. The same techniques as described above can be used to determine the dose prediction model from the remaining treatment plans. For example, an accuracy of the dose prediction model to predict the dose distributions of the remaining treatment plans can be used in an iterative procedure for determining the dose prediction model.

Accordingly, embodiments can compare which patients were good fits and which ones were not that good fits. And, then that information can be used as a criteria to exclude some treatment plans from the model. Additional criteria can also be specified, which can lead to the exclusion of treatment plans. For example, a physician can determine that certain healthy tissue is not need to be spared, and thus treatment plans that were developed to spare the healthy tissue can be excluded. For instance, it may not be important to spare the parotids as the person is already paralyzed, and they are not important to save.

IV. Real-Time Modeling

In some embodiments, a dose prediction model can be made specifically for a new patient. Thus, instead of determining which predetermined model should be chosen, a model that is tailored to the new patient can be created. The new dose prediction model is created from treatment plans that have similar characteristics as the characteristics for the new patient. Accordingly, a similar framework as described above can be used.

For example, if the user knows that the model is to be used for a particular patient, then one does not need to use patients that are very different from the new patient. Instead, information about a new patient can be used to identify a particular D-dimensional point, and a cluster of treatment plans can be identified around that D-dimensional point.

Figure 6:
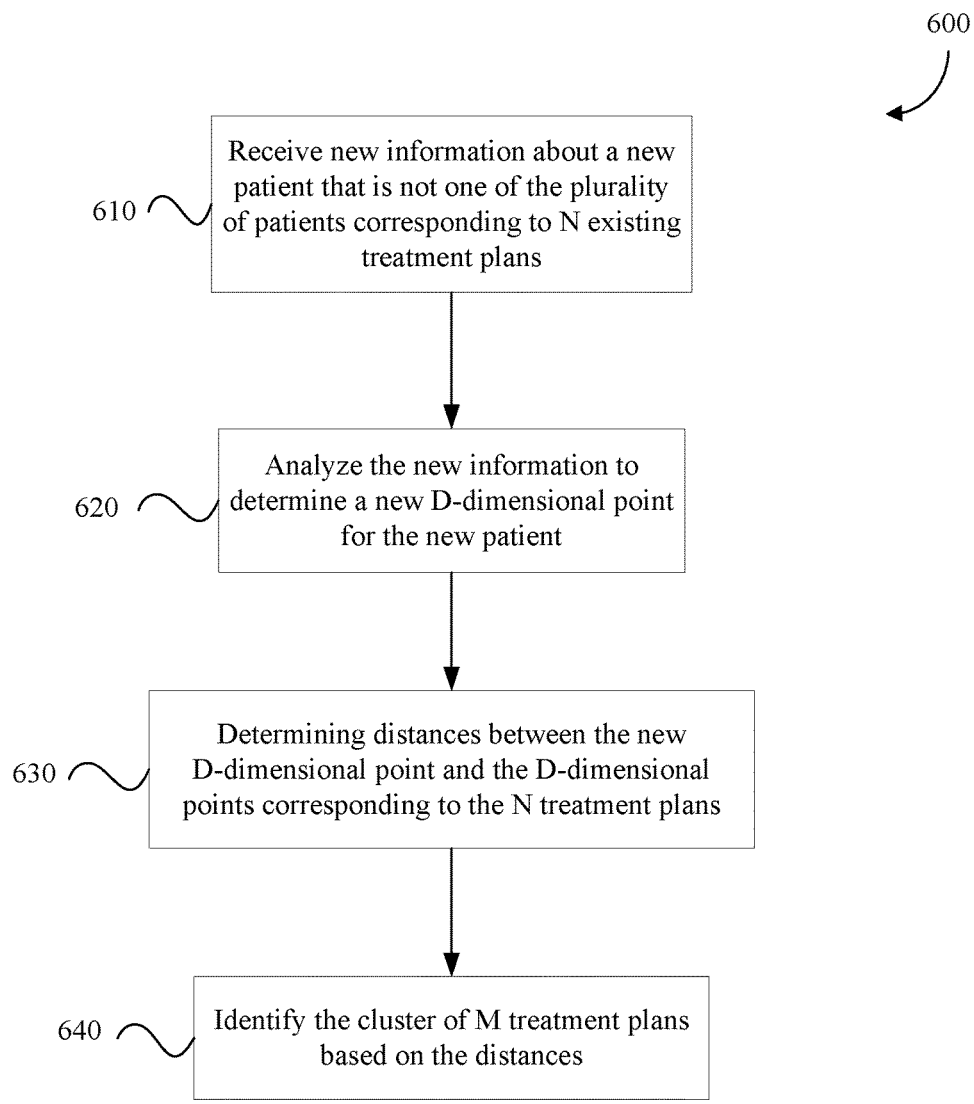
FIG. 6 is a flowchart of method 600 for creating a dose prediction model for new patient according to embodiments of the present invention.

FIG. 6 is a flowchart of method 600 for creating a dose prediction model for new patient according to embodiments of the present invention. Method 600 can be used to perform the clustering of M treatment plans based on the D-dimensional points and block 340 of method 300. For a new patient, the characteristics values would generally not include a dose distribution, as can be done when clustering similar existing treatment plans.

At block 610, new information is received about a new patient that is not one of the plurality of patients corresponding to N existing treatment plans. The information about the new patient can include information as described herein. For example, information about the geometry of the patient (e.g., height and weight), demographic information about the patient, a type of radiation treatment to be used, and relative geometry information about the location of the tumor relative to healthy tissue. Certain information about the new patient corresponds to characteristics for determining a D-dimensional point, as described herein.

At block 620, the new information is analyzed to determine a new D-dimensional point for the new patient. A similar procedure as described above can be used to identify D characteristics of the new information. Then, the values of the D characteristics can be used to create the new D-dimensional point. The particular characteristics to be used can be set as a default, by user, be determined dynamically, or any combination thereof.

At block 630, distances between the new D-dimensional point and the D-dimensional points corresponding to the N treatment plans are determined. In one embodiment, a distance between two points can be calculated as a sum of the differences in the values for each dimension. In another embodiment, different weights can be used for the differences of different dimensions.

For example, a first dimension (e.g., tumor size) can be more important than a second dimension (e.g., demographic information), and thus similarity in values for the first dimension is more critical than a similarity in values for a second dimension. The result can provide a larger weight for multiplying a difference in the values for the first dimension then further weight for multiplying a difference in the values for the second dimension. Additionally, a particular dimension can be required to have the same value as for the new patient, and thus any difference for such dimension can be scaled by a very large number so that the effect a distance is large, thereby preventing points having such differences from being included within the cluster for the new patient. Such weighting schemes can effectively provide a metric for the D-dimensional space, with a metric differs from an identity metric when different weights are used for different dimensions.

At block 640, the cluster of M treatment plans is identified based on the distances. This cluster of M treatment plans can correspond to the cluster determined at block 340 of method 300. In one embodiment, the cluster of M treatment plans corresponds to the M D-dimensional points closest to the new D-dimensional point (e.g., the 30 or 50 treatment plans having D characteristic values closest to the new patient). The value of M can be set as a default, by user, or dynamically. The distance can incorporate any rating scheme described above.

In another embodiment, the M D-dimensional points are the points that are within a specified boundary around the new D-dimensional point. The specified boundary can have any shape, thereby allowing larger differences for certain dimensions. The shape of the boundary can be accounted for by using different metrics for the D-dimensional space. Thus, the boundary can have shape such as a sphere or be oblong. In one implementation, the body can be defined to provide treatment plans that have an exact match for one or more characteristics and that have other characteristics with values that are within a certain percentage of the values for the new patient (e.g., the volume of the tumors from the other treatment plans should be within 30% of the tumor volume for the new patient).

The cluster of M treatment plans can then be used to determine a dose prediction model for generating a new treatment plan for the new patient, as described above (e.g., and block 350 of method 300). Thus, a model can be generated in real-time for the new patient by finding a cluster of M treatment plans that satisfy certain similarity criteria (e.g., the boundary of block 640). For example, a patient image, delineated structures in the body, a defined target, and a prescription for the treatment can be used to find a matching or similar set of plans from existing plans. A learning model can be created out of those plans and used to predict the achievable dose in the new patient. In one aspect, as the treatment plans of the training set are similar, one does not need to use a large training set.

V. Selecting Among Predetermined Models

In some embodiments, a plurality of models are determined from various clusters of similar treatment plans identified from a heterogeneous collection of treatment plans. Such models may be determine an automatic fashion, e.g., as described in method 300. In other implementations, the models may be determined from a manual selection of treatment plans to be used to create each model, or some of the models. Regardless of the technique used to determine the models, an appropriate model can be selected for a new patient from the plurality of predetermined models. If the treatment planning system has many dose prediction models available, it is difficult or time consuming to select a model that is most relevant to the current case.

Each model typically has a certain region where its predictions are valid. If geometric parameters of the new case differ too much from the geometric parameters spanned by the training set used to create the model, the dose predictions are generally not reliable. It is anticipated that a clinic might have several models to cover a large variety of different regions. It is also possible that example treatment plans and models are shared between clinics increasing the available models even more.

Embodiments can automatically select the appropriate model based on the information from the current case. For example, the information from the current case can be used to deduce the model that could has the best relevance or whose predictions are most reliable. The automatic selection can be based on diagnostic information, such as stage information. As another example, the selection also be based on geometric information of the patient, such as geometric information about the tumor (e.g., location).

Figure 7:
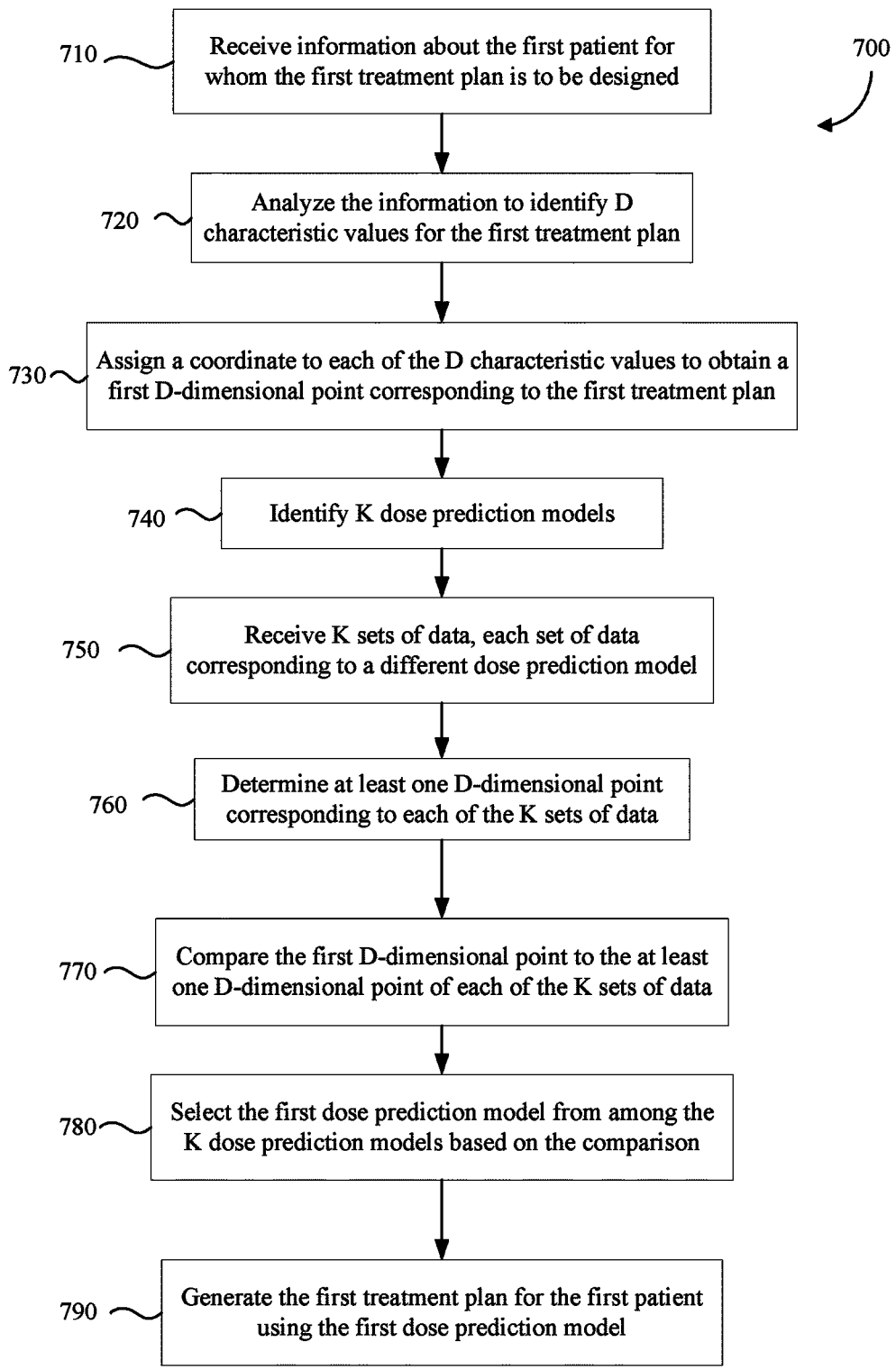
FIG. 7 is a flowchart illustrating a method 700 of selecting a first dose prediction model for generating a dose distribution of a first treatment plan for irradiating a target structure within a first patient according to embodiments of the present invention

FIG. 7 is a flowchart illustrating a method 700 of selecting a first dose prediction model for generating a dose distribution of a first treatment plan for irradiating a target structure within a first patient according to embodiments of the present invention. Aspects of method 700 can be performed in a similar manner as other methods described herein.

At block 710, information is received about the first patient for whom the first treatment plan is to be designed. The information can include geometric information about the patient and/or tumor, diagnostic information, and demographic information. Information about the first treatment plan can also be received. For example, information can be received about the type of radiation treatment to be used.

At block 720, the information is analyzed to identify D characteristic values for the first treatment plan. Each characteristic value corresponds to a different characteristic of the first treatment plan. The analysis can be performed as described above. For example, the D characteristic values can include at least one geometric characteristic value of a tumor of the first patient. In one embodiment, a user can specify which characteristics are to be used, as may be done for other methods described herein.

At block 730, a coordinate is assigned to each of the D characteristic values to obtain a first D-dimensional point corresponding to the first treatment plan. The coordinate can be assigned as described above. Each characteristic can correspond to a different dimension in a D-dimensional space.

At block 740, K dose prediction models are identified. Each dose prediction model is generated from a respective cluster of treatment plans. In one embodiment, some or all of the clusters of treatment plans can be identified using method 300. In another embodiment, some or all of the clusters can be determined manually.

At block 750, K sets of data are received. Each set of data corresponds to a different dose prediction model. A set of data corresponding to a dose prediction model can be generated in various ways. For example, a set of data can be derived from the treatment plans used to create a dose prediction model. The characteristics of the treatment plans of a model can be saved in a variety of ways, e.g., as an average of the characteristics of the treatment plans, as a volume, or as the raw data of the specific treatment plans in the training set of the model. In one embodiment, each set of data includes at least one geometric characteristic value (e.g., a location and/or size of a tumor).

In some implementations, the information from the cluster of treatment plans used to create a dose prediction model can be condensed to one value for each characteristic. This may be done by giving an average of the characteristic values of the treatment plans of the cluster. In other implementations, a set of data can include more than one value for each characteristic, and may include the values for each of the treatment plans of the cluster. In one implementation, the set of data may correspond to characteristic values of representative treatment plans of the cluster.

At block 760, at least one D-dimensional point corresponding to each of the K sets of data is determined. For example, a set of data may be analyzed to extract representative values for the D characteristics. If one representative values obtained for each characteristic, and a single D dimensional point can be obtained for each set of data. In other embodiments, more than one representative value can be obtained, thereby providing multiple D-dimensional points. The multiple D-dimensional points can specify a region of the D-dimensional space. For example, the points can lie on a surface of the D-dimensional shape that defines a region within the surface.

At block 770, the first D-dimensional point is compared to the at least one D-dimensional point of each of the K sets of data. The comparison can be performed in various ways. For example, if each dose prediction model is represented by a single D-dimensional point, distances between the first D-dimensional point and the respective D-dimensional points can be used to identify the closest D-dimensional point to the first D dimensional point. In this manner, the closest dose prediction model can be identified.

As another example when multiple D-dimensional points of a model specify region, it can be determined whether the first D-dimensional point is within a specified region. If the first D-dimensional point is within multiple regions of different models, these identified models can be further analyzed (e.g., a reliability score can be used). In one embodiment, a centroid can be determined from the multiple points of each of the identified models, and a distance of the first D-dimensional point from the centroids can be used in the comparison (e.g., the model having a close a centroid can be identified). In another embodiment, the distance from the first D-dimensional point to a surface of the region can be used. This can test how deep within a region the first D-dimensional point is, and thus the comparison can identify whether the first D-dimensional point is near a surface of the region specified by the points of a model or buried deep within the region, thereby indicating that the first D-dimensional point fits well within the region.

At block 780, the first dose prediction model is selected from among the K dose prediction models based on the comparison. As described above, the model that is the closest to the first D-dimensional point can be selected. Other criteria can be used, e.g., a distance of the first D-dimensional point from a surface of the region corresponding to a dose prediction model. In one aspect, it can be determined that the first treatment plan corresponds to the cluster used to create the first dose prediction model.

At block 790, the first treatment plan is generated for the first patient using the first dose prediction model. For example, the first dose prediction model can be used to predict the dose distribution for the first treatment plan. The predicted dose distribution can be input into an optimization process to determine the parameters of the radiation system. A target structure within the patient can then be irradiated using the new treatment plan.

In one embodiment, the reliability of a model can be used in determining whether to select a model. For example, if two models are identified as being relevant (e.g., based on similarity of the D-dimensional points of the models relative to the first D-dimensional point), then the model with a higher reliability score can be selected. The reliability score can be a measure of accuracy and may be determined as described above. For example, several models may be used to provide a trial-prediction, and the one with the most reliable result is used.

It can happen that the first patient does not correspond to any of the models or corresponds at the same level to two or more models. In one embodiment, the best two or more prediction models can be combined to provide a single prediction model. For example, the treatment plans used to create each of the models can be combined into a single cluster and a new model can be generated from this single, larger cluster. In another embodiment, each of the best two or more models can be selected, and used independently to generate different treatment plans. As an example, this might be done when there are different treatment strategies for the two models, and thus they cannot be combined.

VI. Computer System

Figure 8:
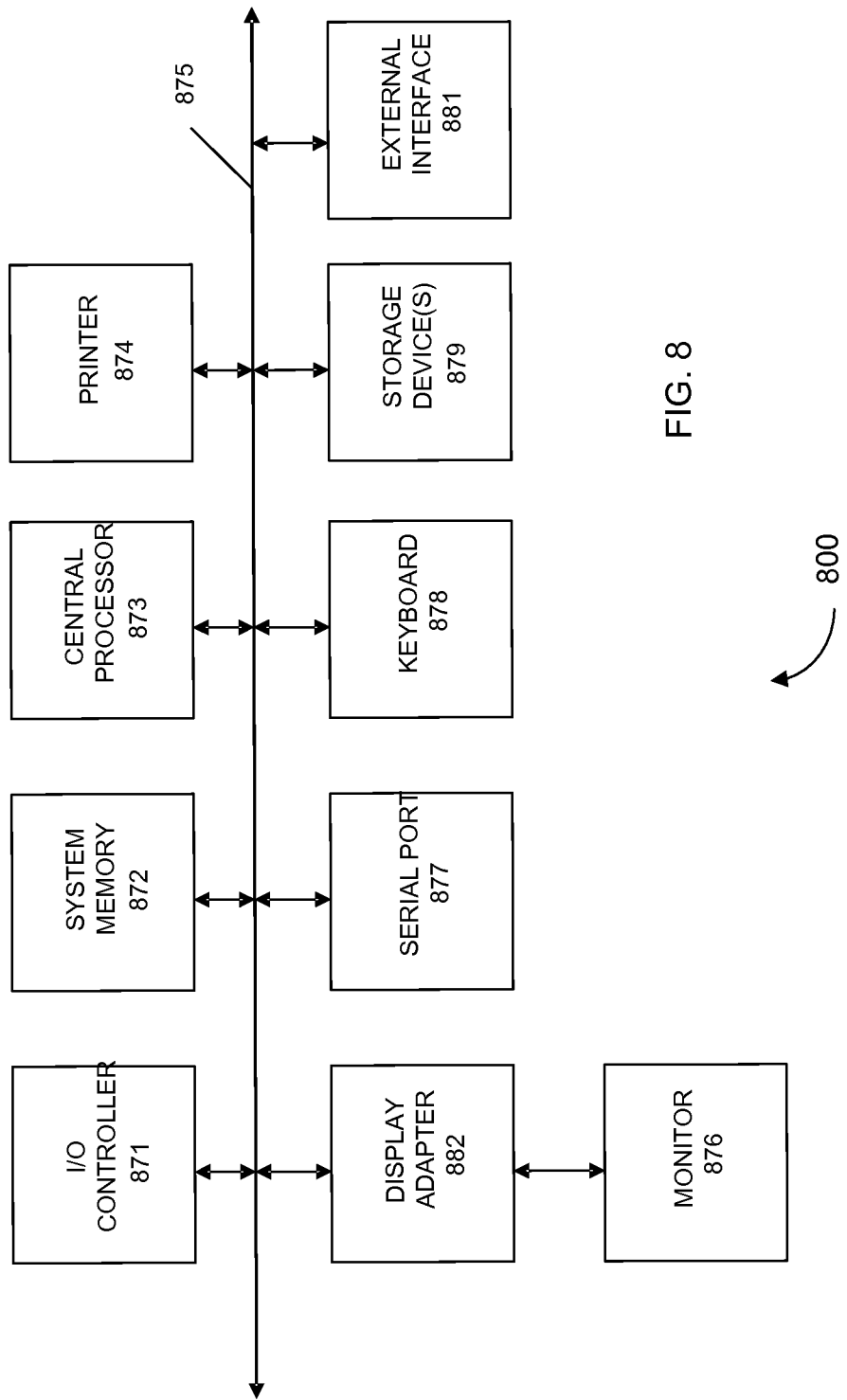
FIG. 8 shows a block diagram of an example computer system 800 usable with system and methods according to embodiments of the present invention.

Any of the computer systems mentioned herein may utilize any suitable number of subsystems. Examples of such subsystems are shown in FIG. 8 in computer apparatus 800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 8 are interconnected via a system bus 875. Additional subsystems such as a printer 874, keyboard 878, storage device(s) 879, monitor 876, which is coupled to display adapter 882, and others are shown. Peripherals and input/output (I/O) devices, which couple to I/O controller 871, can be connected to the computer system by any number of means known in the art, such as serial port 877. For example, serial port 877 or external interface 881 (e.g. Ethernet, Wi-Fi, etc.) can be used to connect computer system 800 to a wide area network such as the Internet, a mouse input device, or a scanner. The interconnection via system bus 875 allows the central processor 873 to communicate with each subsystem and to control the execution of instructions from system memory 872 or the storage device(s) 879 (e.g., a fixed disk, such as a hard drive or optical disk), as well as the exchange of information between subsystems. The system memory 872 and/or the storage device(s) 879 may embody a computer readable medium. Any of the data mentioned herein can be output from one component to another component and can be output to the user.

A computer system can include a plurality of the same components or subsystems, e.g., connected together by external interface 881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of determining a dose prediction model for generating a dose distribution of a radiation treatment plan for irradiating a target structure within a patient, the method comprising:
for each of N radiation treatment plans corresponding to a plurality of former patients treated with a same type of radiation treatment:
receiving information about the radiation treatment plan, including information about a patient for whom the radiation treatment plan was designed and a respective dose distribution;
analyzing, by a computer system, the information to identify D characteristic values of the radiation treatment plan, each characteristic value corresponding to a different characteristic of the radiation treatment plan, the D characteristic values including at least one geometric characteristic value of a tumor of the patient;
assigning, by the computer system, a coordinate to each of the D characteristic values to obtain a D-dimensional point corresponding to the radiation treatment plan, wherein each characteristic corresponds to a different dimension in a D-dimensional space;
identifying, by the computer system, a cluster of M radiation treatment plans based on the D-dimensional points, where M is less than N, and wherein at least two of the M radiation treatments plans in the cluster have a non-zero distance between the respective D-dimensional points;
using the M radiation treatment plans of the cluster to determine a dose prediction model for generating a new radiation treatment plan, wherein when a new patient is assigned to the cluster from among a plurality of clusters of the N radiation treatment plans, the dose prediction model is configured to output a new dose distribution for the new patient using the dose distributions of the M radiation treatment plans in the cluster based on a new D-dimensional point corresponding to the new patient, the new patient being not one of the former patients;
generating the new radiation treatment plan based on the new dose distribution, the new radiation treatment plan including one or more angles of a treatment head and sequence of movements of a multileaf collimator for achieving the new dose distribution; and
providing, by the treatment head coupled with a radiation source, radiation at the one or more angles and using the sequence of movements of the multileaf collimator to specific portions of a treatment area of the new patient according to the new radiation treatment plan.

2. The method of claim 1, wherein identifying a cluster of M radiation treatment plans based on the D-dimensional points includes:
determining distances between the D-dimensional points; and
identifying the cluster of M radiation treatment plans based on the distances.

3. The method of claim 1, further comprising:
identifying K clusters of radiation treatment plans;
determining a respective dose prediction model for each cluster;
receiving information about the new patient;
analyzing the information to determine the new D-dimensional point for the new patient;
using the new D-dimensional point to determine one or more clusters corresponding to the new patient; and
using one or more dose prediction models corresponding to the one or more clusters to determine the new radiation treatment plan for the new patient.

4. The method of claim 3, wherein the one or more clusters are a plurality of clusters, the method further comprising:
for each of the plurality of clusters:
identifying the corresponding dose prediction model;
determining a reliability score of the dose prediction model;
comparing the reliability scores to identify the dose prediction model for determining the new radiation treatment plan.

5. The method of claim 1, wherein identifying a cluster of M radiation treatment plans based on the D-dimensional points includes:
receiving new information about the new patient;
analyzing the new information to determine the new D-dimensional point for the new patient;
determining distances between the new D-dimensional point and each of the D-dimensional points corresponding to the N radiation treatment plans; and
identifying the cluster of M radiation treatment plans based on the distances.

6. The method of claim 5, wherein identifying the cluster of M radiation treatment plans based on the distances includes:
determining the M closest D-dimensional points to the new D-dimensional point; or
determining the M D-dimensional points that are within a specified boundary around the new D-dimensional point.

7. The method of claim 1, wherein the D characteristic values of a radiation treatment plan include a dose distribution of the radiation treatment plan.

8. The method of claim 1, wherein using the M radiation treatment plans of the cluster to determine the dose prediction model includes:
using the M radiation treatment plans to determine an initial dose prediction model;
identifying one or more of the M radiation treatment plans that are not representative of the initial dose prediction model;
removing the identified one or more radiation treatment plans from the cluster;
using the remaining radiation treatment plans of the cluster to determine the dose prediction model.

9. The method of claim 1, wherein using the M radiation treatment plans to determine the dose prediction model includes:
comparing dose distributions of the dose prediction model to dose distributions of the M radiation treatment plans; and
updating the dose prediction model based on the comparison.

10. A computer product comprising a non-transitory computer readable medium storing a plurality of instructions that when executed control a computer system to determine a dose prediction model for generating a dose distribution of a radiation treatment plan for irradiating a target structure within a patient, the instructions comprising:

for each of N radiation treatment plans corresponding to a plurality of former patients treated with a same type of radiation treatment:
receiving information about the radiation treatment plan, including information about a patient for whom the treatment plan was designed and a respective dose distribution;
analyzing the information to identify D characteristic values of the radiation treatment plan, each characteristic value corresponding to a different characteristic of the radiation treatment plan, the D characteristic values including at least one geometric characteristic value of a tumor of the patient; and
assigning a coordinate to each of the D characteristic values to obtain a D-dimensional point corresponding to the radiation treatment plan, wherein each characteristic corresponds to a different dimension in a D-dimensional space;

identifying a cluster of M radiation treatment plans based on the D-dimensional points, where M is less than N, and wherein at least two of the M radiation treatments plans in the cluster have a non-zero distance between the respective D-dimensional points;

using the M radiation treatment plans of the cluster to determine a dose prediction model for generating one or more new radiation treatment plans, wherein when a new patient is assigned to the cluster from among a plurality of clusters of the N radiation treatment plans, the dose prediction model is configured to output a new dose distribution for the new patient using the dose distributions of the M radiation treatment plans in the cluster based on a new D-dimensional point corresponding to the new patient;

generating the new radiation treatment plan based on the new dose distribution, the new radiation treatment plan including angles of a treatment head and sequence of movements of a multileaf collimator for achieving the new dose distribution; and initiating a signal that controls the treatment head and a radiation source to provide radiation at the angles using the sequence of movements of the multileaf collimator to specific portions of a treatment area of the new patient according to the new radiation treatment plan.

11. A radiation therapy system comprising:
a radiation therapy device including:
a rotatable gantry including a treatment head and a multileaf collimator, wherein the multileaf collimator is configured to shape a radiation beam emitted from the radiation head; and
a control unit configured to:
control the rotation of the rotatable gantry;
control emission of the radiation beam from the treatment head; and
control the shape of the radiation beam via the multileaf collimator;
one or more processors; and
a non-transitory computer readable medium storing a plurality of instructions that when executed control the one or more processors to determine a dose prediction model for generating a dose distribution of a radiation treatment plan for irradiating a target structure within a patient, the instructions comprising:

for each of N radiation treatment plans corresponding to a plurality of former patients treated with a same type of radiation treatment:
receiving information about the radiation treatment plan, including information about a patient for whom the treatment plan was designed and a respective dose distribution;
analyzing the information to identify D characteristic values of the radiation treatment plan, each characteristic value corresponding to a different characteristic of the radiation treatment plan, the D characteristic values including at least one geometric characteristic value of a tumor of the patient; and
assigning a coordinate to each of the D characteristic values to obtain a D-dimensional point corresponding to the radiation treatment plan, wherein each characteristic corresponds to a different dimension in a D-dimensional space;

identifying a cluster of M radiation treatment plans based on the D-dimensional points, where M is less than N, and wherein at least two of the M radiation treatments plans in the cluster have a non-zero distance between the respective D-dimensional points;

using the M radiation treatment plans of the cluster to determine a dose prediction model for generating a new radiation treatment plan, wherein when a new patient is assigned to the cluster from among a plurality of clusters of the N radiation treatment plans, the dose prediction model is configured to output a new dose distribution for the new patient using the dose distributions of the M radiation treatment plans in the cluster based on a new D-dimensional point corresponding to the new patient, the new patient being not one of the former patients;

generating the new radiation treatment plan based on the new dose distribution, the new radiation treatment plan including angles of a treatment head and sequence of movements of a multileaf collimator for achieving the new dose distribution; and providing, by the treatment head of the radiation therapy device, radiation at angles and using the sequence of movements of the multileaf collimator to specific portions of a treatment area of the new patient according to the new radiation treatment plan.

12. The radiation therapy system of claim 11, wherein the instructions further comprise:
identifying K clusters of radiation treatment plans;
determining a respective dose prediction model for each cluster;
receiving information about the new patient;
analyzing the information to determine the new D-dimensional point for the new patient;
using the new D-dimensional point to determine one or more clusters corresponding to the new patient; and
using one or more dose prediction models corresponding to the one or more clusters to determine the new radiation treatment plan for the new patient.

13. The radiation therapy system of claim 12, wherein the one or more clusters are a plurality of clusters, wherein the plurality of instructions further comprise:
for each of the plurality of clusters:
identifying the corresponding dose prediction model;
determining a reliability score of the dose prediction model;

comparing the reliability scores to identify the dose prediction model for determining the new radiation treatment plan.

14. The radiation therapy system of claim 11, wherein identifying a cluster of M radiation treatment plans based on the D-dimensional points includes:
receiving new information about the new patient;
analyzing the new information to determine the new D-dimensional point for the new patient;
determining distances between the new D-dimensional point and the D-dimensional points corresponding to the N radiation treatment plans;
identifying the cluster of M radiation treatment plans based on the distances.

15. The radiation therapy system of claim 14, wherein identifying the cluster of M radiation treatment plans based on the distances includes:
determining the M closest D-dimensional points to the new D-dimensional point; or
determining the M D-dimensional points that are within a specified boundary around the new D-dimensional point.

16. The radiation therapy system of claim 11, wherein the D characteristic values of a radiation treatment plan include a dose distribution of the radiation treatment plan.

17. The radiation therapy system of claim 11, wherein using the M radiation treatment plans of the cluster to determine the dose prediction model includes:
using the M radiation treatment plans to determine an initial dose prediction model;
identifying one or more of the M radiation treatment plans that are not representative of the initial dose prediction model;
removing the identified one or more radiation treatment plans from the cluster;
using the remaining radiation treatment plans of the cluster to determine the dose prediction model.

18. The radiation therapy system of claim 11, wherein using the M radiation treatment plans to determine the dose prediction model includes:
comparing dose distributions of the dose prediction model to dose distributions of the M radiation treatment plans; and
updating the dose prediction model based on the comparison.

19. The radiation therapy system of claim 11, wherein identifying a cluster of M radiation treatment plans based on the D-dimensional points includes:
determining distances between the D-dimensional points; and
identifying the cluster of M radiation treatment plans based on the distances.

20. The method of claim 1, wherein the new dose distribution for the new patient is determined as a weighted average of the dose distributions of the M radiation treatment plans in the cluster using weights that depend on distances between the new D-dimensional point to each of the D-dimensional points of the M radiation treatment plans.

* * * * *

UNITED STATES PATENT AND TRADEMARK OFFICE
CERTIFICATE OF CORRECTION

PATENT NO. : 9,827,445 B2  
APPLICATION NO. : 14/040468  
DATED : November 28, 2017  
INVENTOR(S) : Cordero Marcos et al.

Page 1 of 1

It is certified that error appears in the above-identified patent and that said Letters Patent is hereby corrected as shown below:

On the Title Page

Item (57), In the Abstract:
In Line 9, please delete "patient" and insert --the patient--.

In the Claims

In Column 19, Line 37, Claim 1: please delete "treatments" and insert --treatment--.

In Column 20, Line 19, Claim 4: after "model;" please insert --and--.

In Column 20, Line 54, Claim 8: after "cluster;" please insert --and--.

In Column 21, Line 45, Claim 10: after "angles" please insert --and--.

In Column 22, Line 23, Claim 11: please delete "treatments" and insert --treatment--.

In Column 22, Line 67, Claim 13: after "model;" please insert --and--.

In Column 23, Line 12, Claim 14: after "plans;" please insert --and--.

In Column 24, Line 5, Claim 17: after "cluster;" please insert --and--.

Signed and Sealed this  
Twenty-fourth Day of April, 2018

Andrei Iancu  
*Director of the United States Patent and Trademark Office*